United States Patent
Hansford et al.

(10) Patent No.: US 10,188,989 B2
(45) Date of Patent: Jan. 29, 2019

(54) ELECTROOSMOTIC DEVICES FOR FLUID HANDLING

(71) Applicant: OHIO STATE INNOVATION FOUNDATION, Columbus, OH (US)

(72) Inventors: Derek James Hansford, Columbus, OH (US); Jeremiah Schley, Columbus, OH (US); Daniel Gallego-Perez, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 334 days.

(21) Appl. No.: 15/025,443

(22) PCT Filed: Sep. 26, 2014

(86) PCT No.: PCT/US2014/057664
§ 371 (c)(1),
(2) Date: Mar. 28, 2016

(87) PCT Pub. No.: WO2015/048409
PCT Pub. Date: Apr. 2, 2015

(65) Prior Publication Data
US 2016/0228819 A1     Aug. 11, 2016

Related U.S. Application Data

(60) Provisional application No. 61/883,592, filed on Sep. 27, 2013.

(51) Int. Cl.
*G01N 27/453*     (2006.01)
*B01D 61/42*     (2006.01)
(Continued)

(52) U.S. Cl.
CPC ........ *B01D 61/427* (2013.01); *B01L 3/50273* (2013.01); *F04B 19/006* (2013.01);
(Continued)

(58) Field of Classification Search
CPC .......... C12N 2521/00; B81B 2201/036; B81B 2201/058; B01L 3/50273; B01L 2400/0418; F04B 10/006; G01N 27/44791

See application file for complete search history.

(56) References Cited

U.S. PATENT DOCUMENTS 6,406,605 B1 *   6/2002   Moles ........................ F15C 5/00
                                                                                    137/833
7,708,873 B2    5/2010   Bazant et al.
(Continued)

OTHER PUBLICATIONS

Abeyewickreme, Anil, et al. "Bio-electrospraying embryonic stem cells: interrogating cellular viability and pluripotency." Integrative Biology 1.3 (2009): 260-266.
(Continued)

*Primary Examiner* — Alexander S Noguerola
(74) *Attorney, Agent, or Firm* — Meunier Carlin & Curfman LLC (57) ABSTRACT

Disclosed are devices for the controlled handling and delivery of solutions, as well as methods of making and using thereof. The devices can comprise a nanoporous membrane having a top surface and a bottom surface; a fluid source positioned in fluid contact with the bottom surface of the nanoporous membrane; and an electrode patterned on one or more of the surfaces of the nanoporous. membrane (e.g., on the top surface of the nanoporous membrane, on the bottom surface of the nanoporous membrane, or on both the top surface and the bottom surface of the nanoporous membrane). The electrode or electrodes are patterned so as to define a fluid delivery region in fluid contact with the top surface of the nanoporous membrane.

20 Claims, 3 Drawing Sheets

(51) Int. Cl.
*F04B 19/00* (2006.01)
*B01L 3/00* (2006.01)
*G01N 27/447* (2006.01)
*B82Y 30/00* (2011.01)

(52) U.S. Cl.
CPC . *G01N 27/44743* (2013.01); *G01N 27/44791* (2013.01); *B01L 2200/06* (2013.01); *B01L 2300/06* (2013.01); *B01L 2300/0681* (2013.01); *B01L 2400/0418* (2013.01); *B81B 2201/036* (2013.01); *B82Y 30/00* (2013.01); *C12N 2521/00* (2013.01)

(56) References Cited

U.S. PATENT DOCUMENTS

| | | |
|---|---|---|
| 7,799,197 B2 | 9/2010 | Hansford et al. |
| 8,372,629 B2 | 2/2013 | Southern et al. |
| 8,377,277 B2 | 2/2013 | Xie et al. |
| 2004/0178071 A1 | 9/2004 | Harrison et al. |
| 2007/0275455 A1 | 11/2007 | Hung et al. |
| 2010/0160999 A1 | 6/2010 | Epstein et al. |
| 2011/0186449 A1 | 8/2011 | Clochard et al. |
| 2011/0284394 A1 | 11/2011 | Masel et al. |
| 2012/0061240 A1 | 3/2012 | Selvaganapathy et al. |
| 2012/0247980 A1 | 10/2012 | Burke et al. |

OTHER PUBLICATIONS

Agus, David B., et al. "Phase I clinical study of pertuzumab, a novel HER dimerization inhibitor, in patients with advanced cancer." Journal of clinical oncology 23.11 (2005): 2534-2543.
Ai, Ye, et al. "A low-voltage nano-porous electroosmotic pump." Journal of colloid and interface science 350.2 (2010): 465-470.
Allen, Stephanie D., et al. "Peptide vaccines of the HER-2/neu dimerization loop are effective in inhibiting mammary tumor growth in vivo." The Journal of Immunology 179.1 (2007): 472-482.
Brouzes, Eric, et al. "Droplet microfluidic technology for single-cell high-throughput screening." Proceedings of the National Academy of Sciences 106.34 (2009): 14195-14200.
Cameron, M. A., et al. "Atomic layer deposition of SiO2 and TiO2 in alumina tubular membranes: pore reduction and effect of surface species on gas transport." Langmuir 16.19 (2000): 7435-7444.
Chen, Yu-Feng, et al. "Low-voltage electroosmotic pumping using porous anodic alumina membranes." Microfluidics and Nanofluidics 5.2 (2008): 235-244.
Chen, Wei, et al. "Characterization and manipulation of the electroosmotic flow in porous anodic alumina membranes." Analytical chemistry 77.24 (2005): 8102-8108.
Di Carlo, et al. "Dynamic single cell culture array." Lab on a Chip 6.11 (2006): 1445-1449.
Ferrell, Nicholas, et al. "Fabrication of Micro-and Nanoscale Polymer Structures by Soft Lithography and Spin Dewetting." Macromolecular rapid communications 28.8 (2007): 966-971.
Ferrell, Nicholas, et al. "Vacuum-assisted cell seeding in a microwell cell culture system." Analytical chemistry 82.6 (2010): 2380-2386.
Folch, Albert, et al. "Microfabricated elastomeric stencils for micropatterning cell cultures." Journal of biomedical materials research 52.2 (2000): 346-353.
Foy, Kevin C., et al. "Combination treatment with HER-2 and VEGF peptide mimics induces potent anti-tumor and anti-angiogenic responses in vitro and in vivo." Journal of Biological Chemistry 286.15 (2011): 13626-13637.
Foy, Kevin C., et al. "Immunotherapy with HER-2 and VEGF peptide mimics plus metronomic paclitaxel causes superior antineoplastic effects in transplantable and transgenic mouse models of human breast cancer." Oncoimmunology 1.7 (2012): 1004-1016.
Fukuda, Junji, et al. "Micromolding of photocrosslinkable chitosan hydrogel for spheroid microarray and co-cultures." Biomaterials 27.30 (2006): 5259-5267.

Gallego-Perez, Daniel, et al. "High throughput assembly of spatially controlled 3D cell clusters on a micro/nanoplatform." Lab on a chip 10.6 (2010): 775-782.
Gallego-Perez, Daniel, et al. "Micro/nanoscale technologies for the development of hormone-expressing islet-like cell clusters." Biomedical microdevices 14.4 (2012): 779-789.
Garrett, Joan T., et al. "Novel engineered trastuzumab conformational epitopes demonstrate in vitro and in vivo antitumor properties against HER-2/neu." The Journal of Immunology 178.11 (2007): 7120-7131.
Gómez-Sjöberg, Rafael, et al. "Versatile, fully automated, microfluidic cell culture system." Analytical chemistry 79.22 (2007): 8557-8563.
Grothey, Axel. "Recognizing and managing toxicities of molecular targeted therapies for colorectal cancer." Oncology (Williston Park, NY) 20.14 Suppl 10 (2006): 21-28.
Hung, Paul J., et al. "Continuous perfusion microfluidic cell culture array for high-throughput cell-based assays." Biotechnology and bioengineering 89.1 (2005): 1-8.
International Search Report and Written Opinion of the International Searching Authority from Application No. PCT/US2014/057664, dated Dec. 29, 2014, 9 pages.
Kane, Ravi S., et al. "Patterning proteins and cells using soft lithography." Biomaterials 20.23 (1999): 2363-2376.
Karp, Jeffrey M., et al. "Controlling size, shape and homogeneity of embryoid bodies using poly (ethylene glycol) microwells." Lab on a Chip 7.6 (2007): 786-794.
Kaumaya, Pravin TP, et al. "Phase I active immunotherapy with combination of two chimeric, human epidermal growth factor receptor 2, B-cell epitopes fused to a promiscuous T-cell epitope in patients with metastatic and/or recurrent solid tumors." Journal of Clinical Oncology 27.31 (2009): 5270-5277.
Khademhosseini A., et al., "Microscale technologies for tissue engineering and biology." Proc. National Academy of Sciences, 103: 2480-2487, 2006.
Kim, Deok-Ho, et al. "Fabrication of patterned micromuscles with high activity for powering biohybrid microdevices." Sensors and Actuators B: Chemical 117.2 (2006): 391-400.
Kim, Sudong, et al. "Biological applications of microfluidic gradient devices." Integrative Biology 2.11-12 (2010): 584-603.
Lindström, Sara, et al. "Overview of single-cell analyses: microdevices and applications." Lab on a Chip 10.24 (2010): 3363-3372.
Lindström, Sara, et al. "Single-cell culture in microwells." Single-Cell Analysis: Methods and Protocols (2012): 41-52.
Masuda, Hideki, et al. "Ordered metal nanohole arrays made by a two-step replication of honeycomb structures of anodic alumina." science 268.5216 (1995): 1466-1468.
Menon, Vinod P., and et al. "Fabrication and evaluation of nanoelectrode ensembles." Analytical Chemistry 67.13 (1995): 1920-1928.
Miao, J-Y., et al."Micropumps based on the enhanced electroosmotic effect of aluminum oxide membranes." Advanced materials 19.23 (2007): 4234-4237.
Moeller, Hannes-Christian, et al. "A microwell array system for stem cell culture." Biomaterials 29.6 (2008): 752-763.
Nahta, Rita, et al. "Mechanisms of disease: understanding resistance to HER2-targeted therapy in human breast cancer." Nature clinical practice Oncology 3.5 (2006): 269-280.
Patan, Sybill. "Vasculogenesis and angiogenesis as mechanisms of vascular network formation, growth and remodeling." Journal of neuro-oncology 50.1-2 (2000): 1-15.
Pomerantz, Mark M., et al. "Analysis of the 10q11 cancer risk locus implicates MSMB and NCOA4 in human prostate tumorigenesis." PLoS Genet 6.11 (2010): e1001204.
Rosenthal, Adam, et al. "Cell patterning chip for controlling the stem cell microenvironment." Biomaterials 28.21 (2007): 3208-3216.
Roth, Elisabeth A., et al. "Inkjet printing for high-throughput cell patterning." Biomaterials 25.17 (2004): 3707-3715.
Svahn, HA, et al. "Single cells or large populations?" Lab Chip. 7(5): 544-546. 2007.
Theberge, Ashleigh B., et al. "Microdroplets in microfluidics: an evolving platform for discoveries in chemistry and biology." Angewandte Chemie International Edition 49.34 (2010): 5846-5868.

(56) References Cited

OTHER PUBLICATIONS

Thorsen, Todd, et al. "Microfluidic large-scale integration." Science 298.5593 (2002): 580-584.
Unger, Marc A., et al. "Monolithic microfabricated valves and pumps by multilayer soft lithography." Science 288.5463 (2000): 113-116.
Vicari, Daniele, et al. "Engineered conformation-dependent VEGF peptide mimics are effective in inhibiting VEGF signaling pathways." Journal of Biological Chemistry 286.15 (2011): 13612-13625.
Yakar, Shoshana, et al. "The role of the growth hormone/insulin-like growth factor axis in tumor growth and progression: lessons from animal models." Cytokine & growth factor reviews 16.4 (2005): 407-420.
Yang, Chun-Guang, et al. "A radial microfluidic concentration gradient generator with high-density channels for cell apoptosis assay." Lab on a Chip 11.19 (2011): 3305-3312.

* cited by examiner

ELECTROOSMOTIC DEVICES FOR FLUID HANDLING

STATEMENT REGARDING FEDERALLY SPONSORED RESEARCH OR DEVELOPMENT

This invention was made with Government Support under Contract No. EEC-0914790 awarded by the National Science Foundation. The Government has certain rights in the invention.

TECHNICAL FIELD

This application relates to devices for the controlled handling and delivery of solutions, as well as methods of making and using thereof.

BACKGROUND

A major challenge in developing pharmaceutical therapies for diseases such as cancer is to minimize toxicity while maximizing efficacy. Therapies which target the specific biochemical pathways involved in tumor growth and progression offer the potential to provide improved therapeutic efficacy while minimizing side effects.

While targeted therapies, such as those which modulate the biochemical pathways involved in tumor growth and progression, offer great promise for the treatment of diseases such as cancer, many patients become refractory to continued treatment as compensatory pathways become active. In principle, a combination of targeted therapies, which selectively inhibit multiple receptors and their signaling pathways, can be administered to minimize the potential of acquired resistance. By providing a combination of therapies, either simultaneously or in sequence, multiple receptors in a signaling pathway, multiple pathways within the cancer cells, or multiple tissue-level responses can be targeted.

While combination therapies offer tremendous potential, extensive in vitro studies are typically required to identify specific combination therapies which offer improved efficacy. Platforms which can facilitate the in vitro screening of active agents would greatly enhance efforts to develop improved therapeutic regimes.

SUMMARY

Disclosed are devices for the controlled handling and delivery of solutions, as well as methods of making and using thereof. The devices can comprise a nanoporous membrane having a top surface and a bottom surface; a fluid source positioned in fluid contact with the bottom surface of the nanoporous membrane; and an electrode patterned on one or more of the surfaces of the nanoporous membrane (e.g., on the top surface of the nanoporous membrane, on the bottom surface of the nanoporous membrane, or on both the top surface and the bottom surface of the nanoporous membrane). The electrode or electrodes are patterned so as to define a fluid delivery region in fluid contact with the top surface of the nanoporous membrane. The electrode or electrodes can provide a localized electric field across the nanoporous membrane, driving electroosmotic flow of a fluid between the fluid source and the fluid delivery region within the region of the electric field. In this way, the devices can deliver defined volumes of a fluid from the fluid source to the fluid delivery region with precision and accuracy.

In some embodiments, the device can comprise a plurality of fluid delivery regions. For example, the device can comprise a nanoporous membrane having a top surface and bottom surface; one or more fluid sources positioned in fluid contact with the bottom surface of the nanoporous membrane; and one or more electrodes patterned on one of the surfaces of the nanoporous membrane (e.g., on the top surface of the nanoporous membrane, on the bottom surface of the nanoporous membrane, or on both the top surface and the bottom surface of the nanoporous membrane). The electrode or electrodes can be patterned so as to define a plurality fluid delivery regions in fluid contact with the top surface of the nanoporous membrane. The electrode or electrodes can provide a localized electric field across the nanoporous membrane, driving electroosmotic flow of a fluid between the one or more fluid sources and the plurality of fluid delivery regions.

The design and configuration of the components of the devices can be varied depending on the desired performance characteristics of the resulting device. For example, the device can include a single fluid source positioned in fluid contact with the bottom surface of the nanoporous membrane, a plurality of electrodes patterned on the top surface of the nanoporous membrane, and a plurality of electrodes patterned on the bottom surface of the nanoporous membrane. In certain embodiments, the device can comprise two or more parallel linear electrodes patterned on the bottom surface of the nanoporous membrane, and two or more parallel linear electrodes patterned on the top surface of the nanoporous membrane. The two or more parallel linear electrodes patterned on the bottom surface of the nanoporous membrane and the two or more parallel linear electrodes patterned on the top surface of the nanoporous membrane can be substantially orthogonal, so as to form a plurality of areas of overlap at the points where the orthogonal arrays of electrodes intersect. When a voltage is applied between an electrode on the top surface of the nanoporous membrane and an electrode on the bottom surface of the nanoporous membrane, fluid can be selectively delivered only to the fluid delivery region formed by the area of overlap between the two energized electrodes (i.e., the area of the nanoporous membrane which includes both an energized electrode patterned on the top surface of the nanoporous membrane and an energized electrode patterned on the bottom surface of the nanoporous membrane). This can allow for selective delivery of controlled volumes of a fluid exclusively to a particular fluid delivery region of the device.

In some embodiments, the device can include a plurality of fluid sources positioned in fluid contact with the bottom surface of the nanoporous membrane, and a plurality of electrodes patterned on the top surface of the nanoporous membrane so as to define a plurality of fluid delivery regions in fluid contact with the top surface of the nanoporous membrane. The plurality of electrodes can be independently addressable, meaning that the electrodes are not electrically connected. Similarly, the plurality of fluid sources can be independently addressable, meaning that they are not fluidly or electrically connected. By applying a voltage to one or more of the electrodes and grounding the fluid in one or more of the fluid source in fluid contact with the bottom surface of the nanoporous membrane opposite the electrodes, fluid flow can be induced between the grounded fluid source and the fluid delivery region in proximity to the electrode or electrodes to which voltage is applied.

In certain embodiments, the device can comprise two or more parallel microfluidic channels positioned in fluid contact with the bottom surface of the nanoporous membrane, and two or more parallel linear electrodes patterned on the top surface of the nanoporous membrane. The two or more parallel microfluidic channels positioned in fluid contact with the bottom surface of the nanoporous membrane and the two or more parallel linear electrodes patterned on the top surface of the nanoporous membrane can be substantially orthogonal, so as to form a plurality of areas of overlap at the points where the orthogonal arrays of electrodes intersect (i.e., the area of the nanoporous membrane which includes both an electrode patterned on the top surface of the membrane and a microfluidic channel in contact with the bottom of the nanoporous membrane). By applying a voltage to one of the electrodes on the top surface of the nanoporous membrane and grounding the fluid in one of the microfluidic channels positioned in fluid contact with the bottom surface of the nanoporous membrane, fluid can be selectively delivered to the fluid delivery region formed by the area of overlap between the energized electrode and the grounded microfluidic channel (i.e., the area of the nanoporous membrane which includes an energized electrode patterned on the top surface of the membrane and a grounded microfluidic channel positioned in fluid contact with the bottom surface of the nanoporous membrane). This allows for selective delivery of controlled volumes of a fluid exclusively to a particular fluid delivery region of the device.

The devices described herein can be used to deliver defined volumes of solutions to fluid delivery regions containing biological material (e.g., to deliver fluid samples to an array of individual cells or cell clusters present within the fluid delivery regions of a device). The devices can facilitate the handling of the biological material (e.g., facilitate the deposition of the biological material within the fluid delivery regions), and individually deliver small fluid volumes to the fluid delivery regions with a high degree of precision and accuracy. The devices can be used in a variety of applications, including in drug screening assays for pharmaceutical development, in testing of patient cellular responses to drugs for personalized medicine, and to study issues in developmental biology.

DETAILED DESCRIPTION

Figure 1A:
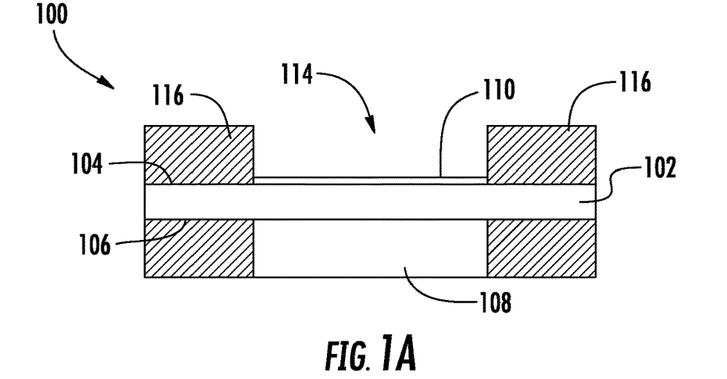
FIGS. 1A-1C are schematic cross-sectional drawings illustrating devices for the controlled handling and delivery of solutions.
Figure 1B:
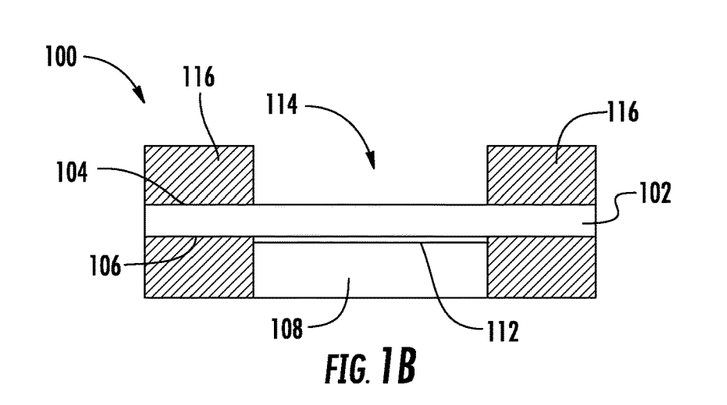
Figure 1C:
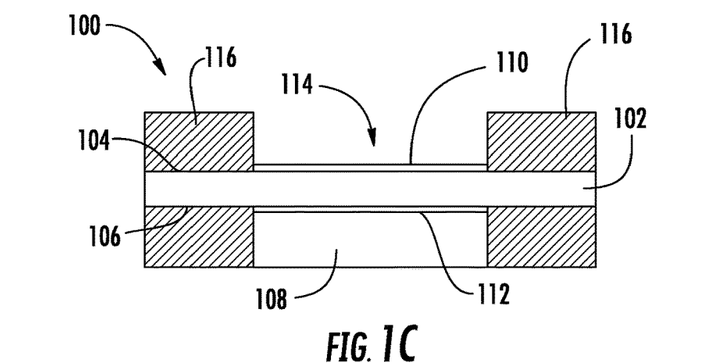

Devices for the controlled handling and delivery of solutions, as well as methods of making and using thereof are provided. The devices provided herein operate using the scientific principle of electroosmotic flow (i.e., the induced flow of an electrolyte liquid due to an applied electric potential across a porous membrane). Referring now to FIGS. 1A-1C, the device (100) can comprise a nanoporous membrane (102) having a top surface (104) and a bottom surface (106); a fluid source (108) positioned in fluid contact with the bottom surface of the nanoporous membrane; and an electrode (110, 112) patterned on one or more of the surfaces of the nanoporous membrane (e.g., on the top surface of the nanoporous membrane (FIG. 1A, 110), on the bottom surface of the nanoporous membrane (FIG. 1B, 112), or on both the top surface and the bottom surface of the nanoporous membrane (FIG. 1B, 110,112)). The electrode or electrodes are patterned so as to define a fluid delivery region (114) in fluid contact with the top surface of the nanoporous membrane. The electrode or electrodes can provide a localized electric field across the nanoporous membrane (102), driving electroosmotic flow of a fluid between the fluid source (108) and the fluid delivery region (114) within the region of the electric field.

The fluid source (108) can be any reservoir which is configured to provide and/or maintain a supply of an electrolyte solution in contact with the bottom surface of the nanoporous membrane. For example, the fluid source can be a delivery chamber into which a fluid is loaded. The delivery chamber can be of any suitable dimensions, so as to conform to device design considerations and provide a suitable volume of fluid for delivery. For example, the delivery chamber can comprise a microfluidic chamber configured to hold fluid volumes of about 5.0 mL or less (e.g., fluid volumes of about 2.5 mL or less, fluid volumes of about 1.0 mL or less, or fluid volumes of about 500 µL or less). The delivery chamber can be fluidly connected to fluid inlets, fluid outlets, microfluidic channels, and other elements to facilitate introduction of a fluid to be delivered into the delivery chamber. In certain embodiments, the delivery chamber comprises a microfluidic chamber which is fluidly connected to one or more microfluidic channels, one or more microfluidic valves, or combinations thereof, which are configured to transport a fluid to be delivered into the microfluidic chamber.

In some embodiments, the fluid source comprises a microfluidic channel. Microfluidic channels are channels within a microfluidic device which form a path, such as a conduit, through which one or more fluids can flow. Suitable microfluidic channels include microfluidic channels which have at least one cross-sectional dimension that is in the range from about 0.1 µm to about 1 millimeter (e.g., from about 1 µm to 1 mm, from about 1 µm to about 750 µm, from about 1 µm to about 500 µm, from about 5 µm to about 500 µm, or from about 5 µm to about 150 µm). For example, the microfluidic channel can have a height and a width. In some embodiments, the microfluidic channel has a height that ranges from about 0.1 µm to about 500 µm (e.g., from about 1 µm to about 500 µm, from about 100 µm to about 500 µm, from about 5 µm to about 500 µm, or from about 5 µm to about 150 µm). In some embodiments, the microfluidic channel has a width that ranges from about 0.1 µm to about 1 mm (e.g., from about 1 µm to about 750 µm, from about 1 µm to about 500 µm, from about 100 µm to about 750 µm, from about 5 µm to about 500 µm, or from about 5 µm to about 150 µm). If desired, the microfluidic channels can have one or more dimensions (e.g., a height, a width, or combinations thereof) of 100 nm or less.

The nanoporous membrane (102) can comprise a porous material which includes a plurality of channels which permeate the porous material, and provide paths for fluid flow across the membrane. The channels can have at least one cross-sectional dimension of less than 1 µm. For example, the channels can have a minimum cross-sectional dimension of from about 2 nm to about 500 nm (e.g., from about 2 nm to about 100 nm, from about 2 nm to about 50 nm, or from about 10 nm to about 30 nm). In some embodiments, the channels have a substantially uniform cross-sectional dimension along their length.

The nanoporous membrane can be formed from a variety of suitable materials, including metal oxides, metal nitrides, and polymers, using methods known in the art. For example, the nanoporous substrate can include a metal oxide, such as tungsten oxide, vanadium oxide, silicon dioxide (silica), common glasses such as silicates, silicon carbide, tantalum oxide, zirconium oxide, hafnium oxide, tin oxide, manganese oxide, titanium oxide, silicon nitride, chromium oxide, aluminum oxide (alumina), zinc oxide, nickel oxide, magnesium oxide, and combinations thereof. The nanoporous substrate can include a polymer, such as polycarbonate (PC), polystyrene (PS), polymethyl methacrylate (PMMA), polydimethylsiloxane (PDMS), cyclic olefin copolymer (COC), and combinations thereof. Suitable nanoporous materials, such as anodized alumina membranes, are also commercially available, for example, from Whatman International, Ltd.

In certain embodiments, the nanoporous membrane can be an anodized alumina (AAO) membrane, a track-etched polycarbonate membrane, a track-etched polystyrene membrane, an anodized silica membrane, a titania membrane, or combinations thereof. In certain embodiments, the nanoporous membrane comprises an anodized alumina membrane. AAO membranes can be formed by electrochemical oxidation of aluminum in acidic solutions to form regular, parallel porous channels. See, for example, H. Masuda and K. Fukuda, *Science,* 268, 1466 (1995); V. P. Menon and CR. Maxim, *Anal. Chem.,* 67, 1920 (1995); and M. A. Cameron, L P. Gartland, J. A. Smith, S. F. Diaz and S. M. George, *Langmuir,* 16, 7435 (2000). The structure of the AAO membrane, include the cross-sectional dimensions of the channels permeating the material, can be varied by altering parameters of the anodization process, including anodization voltage.

The nanoporous substrate can be selected such that the walls of the nanopores permeating the nanoporous substrate have a zeta potential suitable to provide a device having the particular fluid delivery characteristics desired for a particular application. The zeta potential of a nanoporous substrate will vary as a function of the electrolyte solution present (e.g., the solution's chemical composition, ionic strength, and pH) as well as the surface characteristics of the nanoporous substrate. In some embodiments, the nanoporous substrate comprises a material which has a zeta potential, when in contact with 1 mM KCl at pH=7, ranging from about 10 mV to about 200 mV (e.g., from about 20 mV to about 150 mV). In certain embodiments, the nanoporous substrate comprises a material which has a zeta potential, when in contact with 1 mM KCl at pH=7, which ranges from about 30 mV to about 40 mV, from about 40 mV to about 50 mV, from about 75 mV to about 85 mV, from about 85 mV to about 95 mV, or from about 95 mV to about 105 mV.

The thickness of the nanoporous membrane can be varied to provide a device having the particular fluid delivery characteristics desired for a particular application. The membrane can have any suitable thickness, provided that the mechanical properties for the membrane are compatible with device function (e.g., for example, the membrane can have sufficient structural integrity to provide for device assembly and use). In some embodiments, the nanoporous membrane can have a thickness, measured as the distance between the top surface of the nanoporous membrane and the bottom surface of the nanoporous membrane at a point where an electrode is patterned on one or more of the surfaces of the nanoporous membrane, of less than about 75 µm (e.g., less than about 70 µm, less than about 65 µm, less than about 60 µm, less than about 55 µm, less than about 50 µm, less than about 45 µm, less than about 40 µm, less than about 35 µm, less than about 30 µm, less than about 25 µm, less than about 20 µm, less than about 15 µm, less than about 10 µm, or less).

The devices can include one or more electrodes (110, 112) patterned on one or more of the surfaces of the nanoporous membrane. The electrodes can be fabricated from any suitable conductive material, such as a metal (e.g., a noble metal such as gold, silver, or platinum, or silver/silver-chloride), a doped semiconductor, carbon, a conjugated polymer, or metal nitride. The electrode can be fabricated from a material that is conductive and stable within the medium being transported. For example, in embodiments where the device is used in conjunction with a biological sample, the electrode can be fabricated so as to be stable and conductive when in contact with a physiological buffer. The electrodes comprise a thickness and porosity sufficient to provide paths for fluid flow across the electrode. If desired for device function, an insulating layer, such as a thin layer of a non-conductive polymer, can be patterned on top of the electrode or electrodes.

In some embodiments, the device comprises an electrode patterned on the top surface of the nanoporous membrane so as to define a fluid delivery region in fluid contact with the top surface of the nanoporous membrane. By applying a voltage to the electrode on the top surface of the nanoporous membrane and grounding the fluid in fluid source in fluid contact with the bottom surface of the nanoporous membrane opposite the electrode, fluid flow can be induced between the fluid source (108) and the fluid delivery region (114). In these embodiments, the volume of fluid delivered from the fluid source is dependent on several factors, including the voltage applied to the electrode (magnitude and duration), the ionic concentration of fluid being delivered, and the area of overlap between the electrode and the fluid source (i.e., the area of the nanoporous membrane which includes both an electrode patterned on the top surface of the membrane and a fluid source in fluid contact with the bottom of the nanoporous membrane). In these cases, the dimensions of the electrode, the fluid source, or combinations thereof can be selected to provide a fluid delivery region of desired dimensions. The dimensions of the electrode, the fluid source, or combinations thereof can also be selected to influence the volume of fluid delivered from the fluid source to the fluid delivery region.

In some embodiments, the device comprises an electrode patterned on the bottom surface of the nanoporous membrane so as to define a fluid delivery region in fluid contact with the top surface of the nanoporous membrane. By applying a voltage to the electrode on the bottom surface of the nanoporous membrane and grounding fluid present in the fluid delivery region in contact with the top surface of the nanoporous membrane opposite the electrode, fluid flow can be induced between the fluid source (108) and the fluid delivery region (114). In these embodiments, the volume of fluid delivered from the fluid source is dependent on several factors, including the voltage applied to the electrode (magnitude and duration), the ionic concentration of fluid being delivered, and the area of overlap between the electrode and the fluid source (i.e., the area of the nanoporous membrane which includes both an electrode patterned on the bottom surface of the membrane and a grounded fluid in contact with the top of the nanoporous membrane). In these cases, the dimensions of the electrode, the grounded fluid, or combinations thereof can be selected to provide a fluid delivery region of desired dimensions. The dimensions of the electrode, the grounded fluid, or combinations thereof can also be selected to influence the volume of fluid delivered from the fluid source to the fluid delivery region.

In certain embodiments, the device comprises an electrode patterned on the top surface of the nanoporous membrane and an electrode patterned on the bottom surface of the nanoporous membrane so as to define a fluid delivery region in fluid contact with the top surface of the nanoporous membrane. By applying a voltage between the electrodes on the top and bottom surface of the nanoporous membrane, fluid flow can be induced between the fluid source (108) and the fluid delivery region (114). In these embodiments, the volume of fluid delivered from the fluid source is dependent on several factors, including the voltage applied to the electrodes (magnitude and duration), the ionic concentration of fluid being delivered, and the area of overlap between the two electrodes (i.e., the area of the nanoporous membrane which includes both an electrode patterned on the top surface of the membrane and a fluid source in fluid contact with the bottom of the nanoporous membrane). In these cases, the dimensions of the electrodes can be selected to provide a fluid delivery region of desired dimensions. The dimensions of the electrodes can also be selected to influence the volume of fluid delivered from the fluid source to the fluid delivery region.

The devices described herein also include a fluid delivery region (114). The fluid delivery region comprises the region of space proximate to the top surface of the nanoporous membrane to which fluid is delivered upon application of bias across a region of the membrane using one or more electrodes. An appropriate configuration for the fluid delivery region can be selected in view of the intended application for the device (e.g., circular microwells to accommodate and sequester individual cells, fiber mats and/or fluid filled regions to accommodate integral tissue samples, etc.). In some cases, the fluid delivery region can include a volume of fluid (e.g., an aqueous solution such as saline, a buffer, liquid growth media, etc.) in fluid contact with the top surface of the nanoporous membrane. The fluid delivery region can optionally comprise one or more of the elements described below.

In some embodiments, the fluid delivery region comprises a microfluidic channel. In these embodiments, the top surface of the nanoporous membrane can form the bottom of a segment of a microfluidic channel. In these embodiments, controlled volumes of a solution can be delivered from a fluid source to the interior of the microfluidic channel. Suitable microfluidic channels include microfluidic channels which have a height, width, or combination thereof ranging from about 0.1 µm to about 10 mm (e.g., from about 1 µm to about 5 mm, from about 1 µm to 1 mm, from about 1 µm to about 750 µm, from about 1 µm to about 500 µm, from about 5 µm to about 500 µm, or from about 5 µm to about 150 µm). The microfluidic channel can be fluidly connected to one or more additional microfluidic elements (e.g., microfluidic valves, microfluidic chambers, microfluidic mixing elements, microfluidic multiplexers, fluid inlets, fluid outlets, or combinations thereof) and/or one more analytical instruments depending on the desired application of the device.

In some embodiments, the fluid delivery region comprises a microwell. The microwell can be, for example, a depression or well comprising a bottom and one or more side walls (116, FIGS. 1A-1C). In these embodiments, the top surface of the nanoporous membrane can form all or a portion of the bottom of the microwell. The side walls of the microwells can be fabricated from any suitable material. Examples of suitable materials include non-conductive polymers, such as polycarbonate, tetrafluoroethylene, polystyrene, polymethyl methacrylate, polydimethylsiloxane, cyclic olefin copolymer, polyurethanes, polyesters, polyolefins, and combinations thereof.

The microwells can possess one or more dimensions, including height, volume, and/or one or more cross-sectional dimensions, of less than 1000 µm. The shape and dimensions of the microwell can be varied in view of the intended application for the device. For example, the microwells can have a circular horizontal cross-section with a diameter ranging from about 5 µm to about 25 µm (e.g., about 15 µm) for sequestering individual cells to which volumes of fluid are delivered. In other embodiments, microwells can have a circular horizontal cross-section with a diameter ranging from about 125 µm to about 175 µm (e.g., about 150 µm) for culturing and/or sequestering cell spheroids (e.g., for the formation and study of microtumors).

If desired for a particular application, microwells can have a non-circular horizontal cross-section (e.g., a triangular, square, rectangular, polygonal, or oval cross-section). In certain embodiments, the microwell has a circular horizontal cross-section. The circular microwell can have a horizontal cross-sectional diameter of at least about 2 µm (e.g., at least about 5 µm, at least about 10 µm, at least about 25 µm, at least about 50 µm, at least about 100 µm, at least about 500 µm, at least about 1 mm, at least about 2.5 mm, at least about 5 mm, or at least about 7.5 mm). The circular microwell can have a horizontal cross-sectional diameter of about 10 mm or less (e.g., about 7.5 mm or less, about 5 mm or less, about 2.5 mm or less, about 1 mm or less, about 500 µm or less, about 100 µm or less, about 50 µm or less, about 25 µm or less, about 10 µm or less, or about 5 µm or less).

The circular microwell can have a horizontal cross-sectional diameter ranging from any of the minimum values described above to any of the maximum values described above. For example, the circular microwell can have a horizontal cross-sectional diameter ranging from about 2 µm to about 10 mm (e.g., from about 2 µm to about 500 µm, or from about 10 µm to about 500 µm).

In some embodiments, the microwell can have a volume of at least about 2 fL (e.g., at least about 5 fL, at least about 10 fL, at least about 15 fL, at least about 20 fL, at least about 25 fL, at least about 50 fL, at least about 100 fL, at least about 500 fL, at least about 1 nL, at least about 10 nL, at least about 25 nl, at least about 50 nL, at least about 100 nL, at least about 500 nL, at least about 1 µL, at least about 10 µL, at least about 25 µL, at least about 50 µL, at least about 100 µL, or at least about 500 µL). In some embodiments, the microwell can have a volume of about 1 mL or less (e.g., about 500 µL or less, about 100 µL or less, about 50 µL or less, about 25 µL or less, about 10 µL or less, about 1 µL or less, about 500 nL or less, about 100 nL or less, about 50 nL or less, about 25 nL or less, about 10 nL or less, about 1 nL or less, about 500 fL or less, about 100 fL or less, about 50 fL or less, about 25 fL or less, about 20 fL or less, about 15 fL or less, about 10 fL or less, or about 5 fL or less).

The microwell can have a volume ranging from any of the minimum values described above to any of the maximum values described above. For example, the microwell can have a volume of from about 2 fL to about 1 mL (e.g., from about 20 fL to about 1 µL).

The fluid delivery region can comprise a culture matrix. Culture matrices can include a plurality of regions or wells which are interconnected by channels, so as to form a two- or three-dimensional matrix for the culture of cells or tissue. The dimensions of the regions or wells, the dimensions of the interconnecting channels, and the overall morphology of the culture matrix can be selected in view of the cells or tissue being supported and/or cultured within the matrix.

The fluid delivery region can comprise a substrate material. Substrate materials include solid and/or semisolid materials which can be patterned on the top surface of the nanoporous membrane. Examples of suitable substrate materials include gels (e.g., polymer or copolymer hydrogels including aminodextran, dextran, DEAE-dextran, chondroitin sulfate, dermatan, heparan, heparin, chitosan, polyethyleneimine, polylysine, dermatan sulfate, heparan sulfate, alginic acid, pectin, carboxymethylcellulose, hyaluronic acid, agarose, carrageenan, starch, polyvinyl alcohol, cellulose, polyacrylic acid, poly(meth) acrylates, poly meth(methacrylate) PMMA, polyacrylamide, polyhydroxyalkanoates (PHA and PHB), polycaprolactone, polyetheretherketone, polyglycolide, poly-3-hydroxybutyrate, polyethylene glycol, and blends and copolymers thereof), fiber mats (e.g., webs of electrospun polymer fibers), perforated sheets (e.g., plastic sheets or thin films containing one or more perforations, holes, or channels), growth medium, fabric (e.g., non-woven or woven fabrics), foams, decellularized tissue, and combinations thereof. In certain embodiments, the fluid delivery region can comprise a substrate material patterned within a microwell, microfluidic channel, or combinations thereof.

The fluid delivery region can comprise a biological material. The biological material can include, for example, eukaryotic cells, prokaryotic cells, viruses, cell aggregates, tissues, and combinations thereof. In certain embodiments, the fluid delivery region can comprise a biological material deposited on or within a substrate material, a microwell, microfluidic channel, or combinations thereof.

In some embodiments, the device can comprise a plurality of fluid delivery regions. For example, the device can comprise a nanoporous membrane having a top surface and bottom surface; one or more fluid sources positioned in fluid contact with the bottom surface of the nanoporous membrane; and one or more electrodes patterned on one of the surfaces of the nanoporous membrane (e.g., on the top surface of the nanoporous membrane, on the bottom surface of the nanoporous membrane, or on both the top surface and the bottom surface of the nanoporous membrane. The electrode or electrodes are patterned so as to define a plurality fluid delivery regions in fluid contact with the top surface of the nanoporous membrane. The electrode or electrodes can provide a localized electric field across the nanoporous membrane, driving electroosmotic flow of a fluid between the one or more fluid sources and the plurality of fluid delivery regions. In some cases, when a potential bias is applied across the nanoporous membrane, a plurality of fluid delivery regions are fluidly connected to each fluid source in the device.

The design and configuration of the components of the devices can be varied depending on the desired performance characteristics of the resulting device. For example, the device can include a single fluid source positioned in fluid contact with the bottom surface of the nanoporous membrane, and a plurality of electrodes patterned on the top surface of the nanoporous membrane so as to define a plurality of fluid delivery regions in fluid contact with the top surface of the nanoporous membrane. The plurality of electrodes can be independently addressable, meaning that the electrodes are not electrically connected. By applying a voltage to one or more of the electrodes and grounding the fluid in fluid source in fluid contact with the bottom surface of the nanoporous membrane opposite the electrodes, fluid flow can be induced between the fluid source and the fluid delivery region in proximity to the electrode or electrodes to which voltage is applied.

The device can include a single fluid source positioned in fluid contact with the bottom surface of the nanoporous membrane, and a plurality of electrodes patterned the bottom surface of the nanoporous membrane so as to define a plurality of fluid delivery regions in fluid contact with the top surface of the nanoporous membrane. The plurality of electrodes can be independently addressable, meaning that the electrodes are not electrically connected. By applying a voltage to the electrode on the bottom surface of the nanoporous membrane and grounding fluid present in the fluid delivery region in contact with the top surface of the nanoporous membrane opposite the electrode, fluid flow can be induced between the fluid source and the fluid delivery region in proximity to the electrode or electrodes to which voltage is applied.

The device can include a single fluid source positioned in fluid contact with the bottom surface of the nanoporous membrane, a plurality of electrodes patterned on the top surface of the nanoporous membrane, and a plurality of electrodes patterned on the bottom surface of the nanoporous membrane. The plurality of electrodes can be independently addressable, meaning that the electrodes on each surface of the nanoporous membrane are not electrically connected. The one or more electrodes patterned on the top surface of the nanoporous membrane and the one or more electrodes on the bottom surface can be aligned (i.e., they can be configured to overlap in defined regions) so as to define a plurality of fluid delivery regions in fluid contact with the top surface of the nanoporous membrane. By applying a voltage between an electrode on the top and an electrode on the bottom surface of the nanoporous membrane, fluid flow can be selectively induced between the fluid source and the fluid delivery region. In these embodiments, the volume of fluid delivered from the fluid source is dependent on several factors, including the voltage applied to the electrodes (magnitude and duration), the ionic concentration of fluid being delivered, and the area of overlap between the two electrodes (i.e., the area of the nanoporous membrane which includes both an electrode patterned on the top surface of the membrane and an electrode patterned on the bottom of the nanoporous membrane). In certain embodiments, each of the electrodes on the top surface of the nanoporous membrane and each of the electrodes on the bottom surface of the nanoporous membrane are independently addressable.

In certain embodiments, such a device can comprise two or more parallel linear electrodes patterned on the bottom surface of the nanoporous membrane, and two or more parallel linear electrodes patterned on the top surface of the nanoporous membrane. The two or more parallel linear electrodes patterned on the bottom surface of the nanoporous membrane and the two or more parallel linear electrodes patterned on the top surface of the nanoporous membrane can be substantially orthogonal, so as to form a plurality of areas of overlap at the points where the orthogonal arrays of electrodes intersect. In these cases, when a voltage is applied between an electrode on the top and an electrode on the bottom surface of the nanoporous membrane, fluid can be selectively delivered only to the fluid delivery region formed by the area of overlap between the two energized electrodes (i.e., the area of the nanoporous membrane which includes both an energized electrode patterned on the top surface of the nanoporous membrane and an energized electrode patterned on the bottom surface of the nanoporous membrane). This allows for selective delivery of controlled volumes of a fluid exclusively to a particular fluid delivery region of the device.

In some embodiments, the device can include a plurality of fluid sources positioned in fluid contact with the bottom surface of the nanoporous membrane, and a plurality of electrodes patterned on the top surface of the nanoporous membrane so as to define a plurality of fluid delivery regions in fluid contact with the top surface of the nanoporous membrane. The plurality of electrodes can be independently addressable, meaning that the electrodes are not electrically connected. Similarly, the plurality of fluid sources can be independently addressable, meaning that they are not fluidly or electrically connected. By applying a voltage to one or more of the electrodes and grounding the fluid in one or more of the fluid source in fluid contact with the bottom surface of the nanoporous membrane opposite the electrodes, fluid flow can be induced between the grounded fluid source and the fluid delivery region in proximity to the electrode or electrodes to which voltage is applied.

Figure 2:
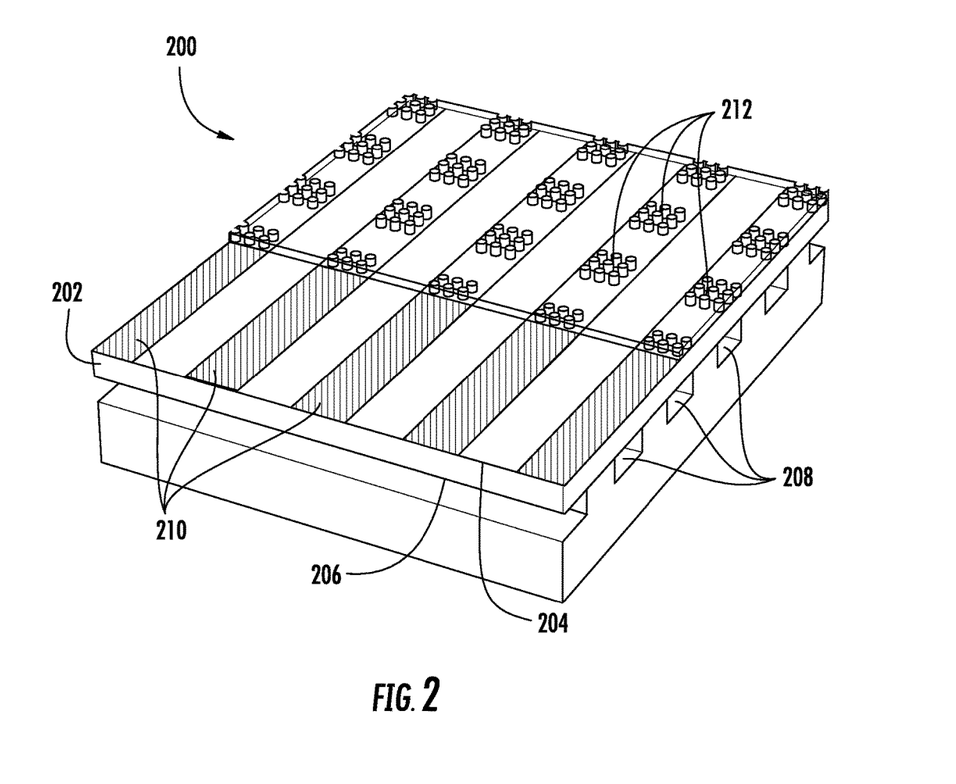
FIG. 2 is a schematic drawing illustrating a device for the controlled handling and delivery of solutions which includes a plurality of fluid delivery regions.

Referring now to FIG. 2, in certain embodiments, the device (200) can comprise a nanoporous membrane (202) having a top surface (204) and bottom surface (206); a plurality of fluid sources (208) positioned in fluid contact with the bottom surface of the nanoporous membrane; a plurality of electrodes (210) patterned on one or more of the surfaces of the nanoporous membrane (e.g., on the top surface of the nanoporous membrane, on the bottom surface of the nanoporous membrane, or on both the top surface and the bottom surface of the nanoporous membrane). The plurality of electrodes are patterned so as to define a plurality fluid delivery regions (212) in fluid contact with the top surface of the nanoporous membrane.

As shown in FIG. 2, in some embodiments, the plurality of fluid sources (208) positioned in fluid contact with the bottom surface of the nanoporous membrane comprises a plurality of microfluidic channels. In these embodiments, the bottom surface of the nanoporous membrane can comprise the top (or ceiling) of the microfluidic channels, such that fluid present within the microfluidic channels is positioned in fluid contact with the bottom of the nanoporous membrane. In some embodiments, the plurality of fluid sources (208) positioned in fluid contact with the bottom surface of the nanoporous membrane comprises a plurality of parallel microfluidic channels. As shown in FIG. 2, in some embodiments, the plurality of electrodes (210) patterned on one or more of the surfaces of the nanoporous membrane comprises a plurality of electrodes (e.g., parallel linear electrodes) patterned on the top surface of the nanoporous membrane.

As shown in FIG. 2, in some embodiments, the device can comprise a plurality of fluid delivery regions configured as a matrix. The matrix can comprise two or more rows of fluid delivery regions, each row of fluid delivery regions comprising a plurality of fluid delivery regions; and two or more columns of fluid delivery regions, each column of fluid delivery regions comprising a plurality of fluid delivery regions. In certain embodiments, such a device comprises two or more parallel microfluidic channels positioned in fluid contact with the bottom surface of the nanoporous membrane, and two or more parallel linear electrodes patterned on the top surface of the nanoporous membrane. The two or more parallel microfluidic channels positioned in fluid contact with the bottom surface of the nanoporous membrane and the two or more parallel linear electrodes patterned on the top surface of the nanoporous membrane can be substantially orthogonal as shown in FIG. 2, so as to form a plurality of areas of overlap at the points where the orthogonal arrays of electrodes intersect (i.e., the area of the nanoporous membrane which includes both an electrode patterned on the top surface of the membrane and a microfluidic channel in contact with the bottom of the nanoporous membrane). In these cases, by applying a voltage to one of the electrodes on the top surface of the nanoporous membrane and grounding the fluid in one of the microfluidic channels positioned in fluid contact with the bottom surface of the nanoporous membrane, fluid can be selectively delivered only to the fluid delivery region formed by the area of overlap between the energized electrode and the grounded microfluidic channel (i.e., the area of the nanoporous membrane which includes an energized electrode patterned on the top surface of the membrane and a grounded microfluidic channel positioned in fluid contact with the bottom surface of the nanoporous membrane). This allows for selective delivery of controlled volumes of a fluid exclusively to a particular fluid delivery region of the device.

The devices described above can further include a controller including a power source electrically connected to the one or more electrodes in the device. The controller can be configured to apply a potential bias (e.g., applied by means of a direct current or an alternating current) effective to induce fluid flow across the nanoporous membrane. For example, the controller can be configured to apply a potential bias of from about −0.8V to about 0.8V across the nanoporous membrane.

Also provided are methods of fabricating the devices described herein. Methods of fabricating the devices described herein can comprise providing a nanoporous membrane having a top surface and a bottom surface; patterning one or more electrodes on the top surface of the nanoporous membrane, bottom surface of the nanoporous membrane, or both the top and bottom surface of the nanoporous membrane; forming and/or positioning one or more fluid sources in fluid contact with the bottom surface of the nanoporous membrane; and optionally fabricating one or more elements within the one or more fluidly delivery regions of the device (e.g., forming one or more microwells, patterning one or more substrate materials, etc.).

The one or more electrodes can be patterned on the nanoporous membrane using any suitable technique for the micropatterning of conductive materials on a surface. For example, the one or more electrodes can be patterned using a lift-off deposition method. In the lift-off deposition method, lithography is used to define the negative pattern of the electrode in a polymer layer surface of the nanoporous membrane. A conductive material (e.g., a metal such as gold) is then evaporated onto the nanoporous membrane and polymer. The assembly can then be soaked in a solvent (e.g., acetone) with brief ultrasonication to dissolve the patterned polymer, leaving behind only the conductive material deposited directly onto the surface of the nanoporous membrane.

One or more fluid sources can then be formed and/or positioned in fluid contact with the bottom surface of the nanoporous membrane. For example, in some embodiments, the one or more fluid sources comprise microfluidic channels. The microfluidic channels, along with other microfluidic elements in fluid communication with the microfluidic elements, can be fabricated using standard soft lithography techniques known in the art. See, for example, Unger, M. A., et al. Science, 288:113-116 (2000) and Thorsen, T., et al. Science, 298:580-584 (2002). The microfluidic channels can be fabricated from a number of materials including, but not limited to glass, SU-8 epoxy resin, polydimethylsiloxane (PDMS), polymethyl methacrylate (PMMA), polyurethane methacrylate (PUMA), theromset polyesters, polythiols, polyethylenes, polysilanes, and other polymers known in the art. Several general methods exist to fabricate microfluidic channels including, but not limited to replica molding (e.g., soft-lithography), hot embossing, injection molding, mechanical micromachining, and laser micromachining Once formed, the microfluidic channels can be positioned in fluid contact with the bottom surface of the nanoporous membrane. Positioning can involve applying a thin layer of an adhesive or curing polymer (e.g., PDMS) onto the top of the microfluidic sheet containing the microfluidic channels, placing the top of the microfluidic sheet in contact with the bottom surface of the nanoporous membrane, and applying gentle pressure between the microfluidic sheet and the nanoporous membrane until the adhesive is set or the curing polymer cured. Finally, one or more elements can be formed within the one or more fluidly delivery regions of the device (e.g., forming one or more microwells, patterning one or more substrate materials, etc.) using standard microfabrication techniques.

Also provided are methods of using the devices described herein. Provided are methods for delivering a defined volume of a solution to a fluid delivery region. The methods can include providing a solution to be delivered in a fluid source of the device defined described; and applying a potential bias across the nanoporous membrane for a period of time to induce flow of the solution from the fluid source to the fluid delivery region. The potential bias and period of time are selected to induce the flow of a defined volume of the solution from the fluid source to the fluid delivery region.

In some embodiments, the device comprises a first fluid delivery region and a second fluid delivery region. In such cases, methods can comprise delivering a first volume of the solution to the first fluid delivery region and delivering a second volume of the solution to the second fluid delivery region. In certain embodiments, the first volume is different from the second volume (e.g., the first volume is greater than the second volume, or the first volume is less than the second volume).

The volume of fluid delivered from the fluid source is dependent on several factors, including the voltage applied to the electrode (magnitude and duration), the ionic concentration of fluid being delivered, and the area of overlap between the electrode and the fluid source (i.e., the area of the nanoporous membrane which includes both an electrode patterned on the bottom surface of the membrane and a grounded fluid in contact with the top of the nanoporous membrane) or the area of overlap between the two electrodes (i.e., the area of the nanoporous membrane which includes both an electrode patterned on the top surface of the membrane and a fluid source in fluid contact with the bottom of the nanoporous membrane).

The devices described herein can be used to deliver defined volumes of a solution with accuracy and precision. The potential bias and period of time are selected to induce the flow of a defined volume of the solution from the fluid source to the fluid delivery region. In some embodiments, the defined volume of solution is at least about 1 fL (e.g., at least about 5 fL, at least about 10 fL, at least about 15 fL, at least about 20 fL, at least about 25 fL, at least about 50 fL, at least about 100 fL, at least about 500 fL, at least about 1 nL, at least about 10 nL, at least about 25 nl, at least about 50 nL, at least about 100 nL, or at least about 500 nL). In some embodiments, the defined volume of solution is about 1 µL or less (e.g., about 500 nL or less, about 100 nL or less, about 50 nL or less, about 25 nL or less, about 10 nL or less, about 1 nL or less, about 500 fL or less, about 100 fL or less, about 50 fL or less, about 25 fL or less, about 20 fL or less, about 15 fL or less, about 10 fL or less, or about 5 fL or less). The defined volume of solution can range from any of the minimum values described above to any of the maximum values described above. For example, the volume of solution can range from about 1 fL to about 1 µL (e.g., from about 1 fL to about 1 nL).

The potential bias, ionic concentration of fluid being delivered, and device configuration can be selected to induce fluid flow between the fluid source and the fluid delivery regions at a desired flow rate for a particular application. Defined flow rates can be used, for example, for studies of shear on cells. In some embodiments, the potential bias, ionic concentration of fluid being delivered, and device configuration can be selected to provide a fluid flow rate ranging from about 0.01 fL/ms to about 1 pL/ms (e.g., from about 0.025 fL/ms to about 500 fl/ms, from about 0.025 fL/ms to about 100 fl/ms, from about 0.025 fL/ms to about 10 fl/ms, from about 0.025 fL/ms to about 1 fl/ms, from about 0.025 fL/ms to about 0.5 fl/ms, from about 0.025 fL/ms to about 0.075 fl/ms, or from about 0.10 fL/ms to about 0.50 fl/ms). In some embodiments, the potential bias, ionic concentration of fluid being delivered, and device configuration can be selected to provide a fluid flow rate, in terms of fluid velocity, ranging from about 0.1 microns per second to about 10 microns per second.

In certain embodiments, the fluid delivery region can comprise a biological material (e.g., eukaryotic cells, prokaryotic cells, viruses, cell aggregates, tissues, and combinations thereof). Accordingly, methods can further include the step of depositing a biological material in one or more of the fluid delivery regions of the device. Deposition of the biological material can comprise sedimentation (e.g., allowing the biological materials to settle in the fluid delivery region). Deposition of the biological material can also comprise applying a potential bias across the nanoporous membrane to induce fluid flow from the fluid delivery region to the fluid source. In these cases, fluid flow can draw the biological material into the fluid delivery region. Deposition of the biological material can also comprise generating a pressure gradient across the nanoporous membrane to induce fluid flow from the fluid delivery region to the fluid source (e.g., using microfluidic pumps or other device components to drive fluid flow from the fluid delivery region to the fluid source). In these cases, fluid flow can draw the biological material into the fluid delivery region. Deposition of the biological material can also provide of the biological material within the fluid delivery region. Physical positioning methods can be used, for example, when physical manipulation of the biological material is convenient or desirable (e.g., when the biological material comprises a tissue sample).

When the fluid delivery region comprises a biological material, methods can further include the step of analyzing the biological material. The biological material can be analyzed before the delivery of a volume of fluid to the fluid delivery region, after the delivery of a volume of fluid to the fluid delivery region, or combinations thereof. The biological material can be analyzed using a variety of suitable methods (e.g., using various types of microscopy), for example, to assess the impact of the solution delivered on the biological material (e.g., to determine the efficacy of a drug).

The methods described herein can be used to deliver controlled volumes of a variety of solutions to fluid delivery regions. The exact nature of the solutions will depend upon the intended applications for the device. For example, in some embodiments, the solution being delivered to the fluid delivery region comprises an aqueous solution such as saline, a buffer, liquid growth media, etc. containing an analyte or agent being tested for activity (e.g., biological activity, corrosive activity, chemical reactivity, etc.). In some embodiments, the analyte or agent is selected from the group consisting of therapeutic agents, diagnostic agents, prophylactic agents, nutritional agents, and combinations thereof.

The devices provided herein can be used to conduct pharmacological dosing studies. For example, in the case of a device having a single fluid source positioned in fluid contact with the bottom surface of the nanoporous membrane, two or more parallel linear electrodes patterned on the bottom surface of the nanoporous membrane, two or more parallel linear electrodes patterned on the top surface of the nanoporous membrane, and a plurality of fluid delivery regions defined by the plurality of electrodes in fluid contact with the top surface of the nanoporous membrane, the fluid source can be filled with a solution of an active agent to be investigated, and biological material can be deposited into the plurality of fluid delivery regions in the device. A voltage can applied between a first electrode on the top surface of the nanoporous membrane and a first electrode on the bottom surface of the nanoporous membrane, selectively inducing fluid flow from the fluid source to a first fluid delivery region formed by the area of overlap between the two energized electrodes (i.e., the area of the nanoporous membrane which includes both the first electrode patterned on the top surface of the nanoporous membrane and the first electrode patterned on the bottom surface of the nanoporous membrane). Subsequently, a voltage can applied between a second electrode on the top surface of the nanoporous membrane and a second electrode on the bottom surface of the nanoporous membrane, selectively inducing fluid flow from the fluid source to a second fluid delivery region formed by the area of overlap between the two energized electrodes (i.e., the area of the nanoporous membrane which includes both the second electrode patterned on the top surface of the nanoporous membrane and the second electrode patterned on the bottom surface of the nanoporous membrane). The voltage applied to the second electrodes can differ from the voltage applied to the first electrodes in magnitude and/or duration, such that differing volumes of fluid are delivered to the biological material in the first fluid delivery region and to the biological material in the second fluid delivery region. In this way, a biological material can be contacted with different amounts of an active agent, for example, to evaluate suitable dosages of an active agent for the treatment of a disease and disorder. Such methods could be designed to be similar to conventional pharmaceutical studies; however, they could be designed to use smaller quantities of active agent.

The devices described herein can also be used to evaluate combinations of active agents at varied dosages. Such studies can be performed, for example, using a device which comprises two or more parallel microfluidic channels positioned in fluid contact with the bottom surface of the nanoporous membrane, and two or more parallel linear electrodes patterned on the top surface of the nanoporous membrane. The two or more parallel microfluidic channels positioned in fluid contact with the bottom surface of the nanoporous membrane and the two or more parallel linear electrodes patterned on the top surface of the nanoporous membrane can be substantially orthogonal, so as to form a plurality of areas of overlap at the points where the orthogonal arrays of electrodes intersect (i.e., the area of the nanoporous membrane which includes both an electrode patterned on the top surface of the membrane and a microfluidic channel in contact with the bottom of the nanoporous membrane). Different active agent combinations can be present in each microfluidic channel. By introducing concentration gradients within the microfluiding channels and/or applying different voltages (e.g., in terms of magnitude and/or duration) to the electrodes in the device, varied concentrations of different active agent combinations can be delivered to each fluid delivery region. Such devices can serve as a highly multiplexed array for evaluating combination therapies.

The devices described herein can also be used for personalized drug testing. It is known that individuals (and individual tissues/tumors) can respond differently to active agents. In order to determine an optimal therapeutic regimen for an individual (e.g., an optimized dosage, optimized active agent(s), or combinations thereof), a number of potential therapeutic regimes can be tested in vitro using tissue from the individual. For example, when determining an optimal cancer therapy for a patient, a tumor can be biopsied and digested to separate the tumor cells or cell clusters. The tumor cells or cell clusters can be deposited into the fluid delivery regions of a device described above. For example, a device which comprises two or more parallel microfluidic channels positioned in fluid contact with the bottom surface of the nanoporous membrane, and two or more parallel linear electrodes patterned on the top surface of the nanoporous membrane can be used. The two or more parallel microfluidic channels positioned in fluid contact with the bottom surface of the nanoporous membrane and the two or more parallel linear electrodes patterned on the top surface of the nanoporous membrane can be substantially orthogonal, so as to form a plurality of areas of overlap at the points where the orthogonal arrays of electrodes intersect (i.e., the area of the nanoporous membrane which includes both an electrode patterned on the top surface of the membrane and a microfluidic channel in contact with the bottom of the nanoporous membrane). Different active agent combinations can be present in each microfluidic channel. By introducing concentration gradients within the microfluiding channels and/or applying different voltages (e.g., in terms of magnitude and/or duration) to the electrodes in the device, varied concentrations of different active agent combinations can be delivered to each fluid delivery region. In this way, different cocktails of chemotherapeutics can be tested at different concentrations on the tumor cells or cell clusters, and the effects can be used to determine the most effective therapy which can be administered to the patient.

The devices described herein can also be used, for example, for selective cell placement/loading and release (e.g., to place cells in proximity to complementary cells, for example, to study cell signaling, or to select cells from solution as they flow past), to study stem cell biology/differentiation and controlled release (e.g., by delivering controlled volumes of chemicals to cells to examine the differentiation pathways in embryos), to study treatments involving functional electrical stimulation (FES) and functional chemical stimulation (FCS), to study the effects of cosmic radiation on cellular biology, and for drug development (e.g., to evaluate the efficacy of potential active agent in vitro)

EXAMPLES

Device Description

Figure 3A:
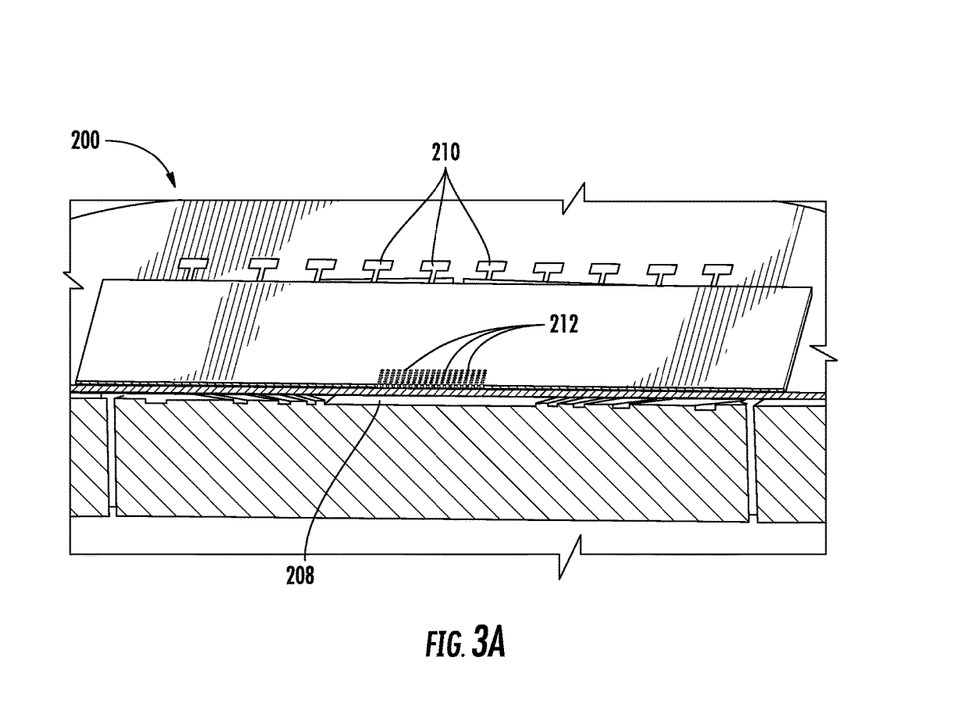
FIGS. 3A-3B are schematic drawings illustrating an example device for the controlled handling and delivery of solutions including 19 electrodes and 19 orthogonal microfluidic channels.
Figure 3B:
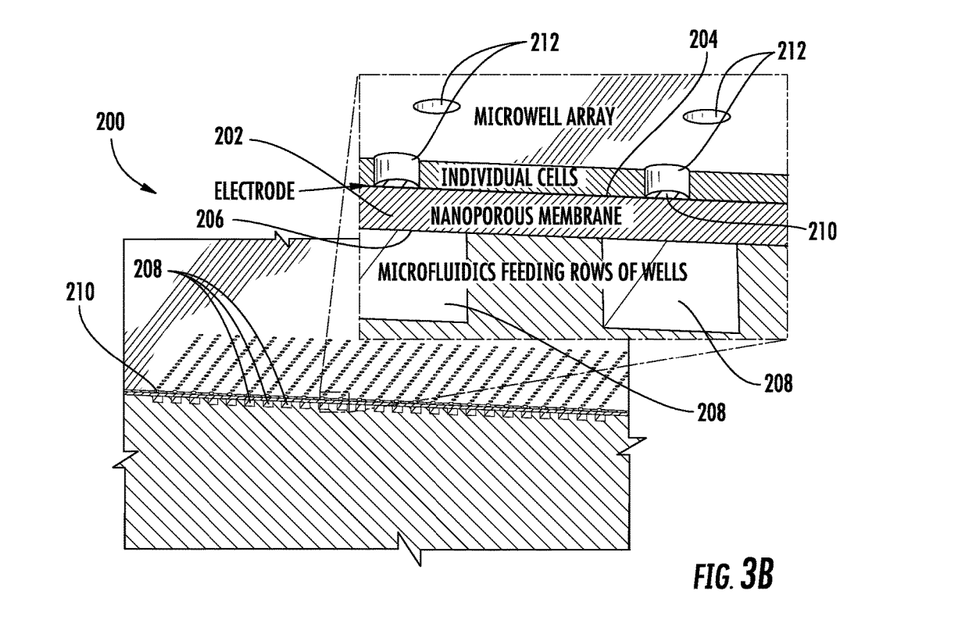

An example device for the controlled handling and delivery of solutions containing 19 electrodes and 19 orthogonal microfluidic channels was fabricated. The device is schematically illustrated in FIGS. 3A and 3B. The intersection of each of the electrodes and the orthogonal microfluidic channels provides a uniquely addressable fluid delivery regions to which fluid flow can be directed. A 3×3 grid of microwells was patterned in each unique fluid delivery region. The resulting device included 361 unique fluid delivery regions and 3259 microwells.

Substrate Preparation

Device substrates were prepared by cleaning 300 micron glass pyrex carrier wafers in piranha bath for 20 minutes or until clean. Pyrex wafers were then dehydrated by baking at 200° C. for one hour. Carrier wafers were then removed and placed into an HMDS oven for 35 minutes. Carrier wafers were removed from oven and air cooled. PDMS was spin coated on to the surface of the carrier wafers at a 1000 RPM for 60 seconds. The PDMS was then baked on a hotplate for 2 minutes at 150° C. Whatman Anodisc™ 200 nm membranes were pressed onto the surface of the PDMS using soft even pressure. Force was roughly distributed using a foam pad from the Anodisc membrane shipping container to even the pressure across the surface. A 10% polyvinyl alcohol solution was spin coated on to the surface of the membrane at 4000 RPM. Samples were then baked on a hotplate for 30 minutes at 60° C.

Photolithography

Photolithography provided for the electrical contacts on the top surface of the device. The features formed in this step allowed for the deposition of metal into a select region that will become the porous electrodes that will define, with the microfluidic channels, the delivery regions The device was spin coated with SPR-220 for 8 seconds at 100 RPM ramping at 100 RPM/s immediately transitioning to 60 s at 1600 RPM with 300 RPM/s. The device was then immediately baked on a hot plate at 115° C. in proximity for 30 seconds, followed immediately by 90 seconds in direct contact with the hot plate. Subsequently, the sample was air cooled in a wafer carrier.

The device was then aligned and exposed using an EVG 620 aligner. The sample was exposed using an 18 second exposure. Following alignment, the sample was removed to a wafer carrier, and incubated for 2 hours to allow water to diffuse back into the SPR-220 thick film. The device was then baked on a hotplate at 115° C. in proximity for 30 seconds, then at 115° C. in direct contact for 90 seconds.

The device was developed in a bath of Microposit MF CD-26 for 90 s after which it was spray developed for 60 seconds. The device was then rinsed in a DI water bath for 60 seconds. Development completion was gauged based on where the Anodisc membrane turns dark. If development was not complete, the spray and water bath process was repeated. Water was removed from membranes using a nitrogen gun. The dried sample was transferred to a hotplate at 90° C. for 20 minutes to further dehydrate the membrane. Optionally, the device can be transferred to a nitrogen oven to dehydrate the membrane and photoresist.

Evaporation

The device was then transferred to a Denton E-beam evaporator. The evaporator was pumped to a vacuum of at least $4\times10^{-6}$ torr. Titanium was soaked in the e-beam for 3 minutes until it was sufficiently melted and evaporating. 2.5 nm of titanium was evaporated at a rate of no more than 0.6 Angstroms/second. Gold was then evaporated after a 3 minute soak to ensure uniform evaporation of material. 77.5 nm of gold was deposited at a rate of no more than 1.1 Angstroms/s. The device was then allowed to cool in vacuum and before removal. This evaporation defined the 19 connection sites and conduction lines (i.e., electrodes) across the surface of the membrane, which will eventually be referenced as the "top side" or patterned side of the membrane.

Liftoff

The device was removed from PDMS carrier by saturating the surface of the membrane with 100° C. N-methyl-2-pyrrilidone (NMP). Fine tip tweezers were inserted under the annular ring of the membrane until the membrane was lifted slightly up from the PDMS. Tweezers were then progressed around the membrane in a circular pattern slowly progressing radially inward to the center of the membrane while allowing NMP to saturate the underside of the membrane. Using this procedure, the membrane simply lifted off once the underside was fully saturated with NMP. The membrane was then transferred to a small dish of clean 100° C. NMP, and soaked for 1 minute or until gold lift off layer begins to fragment. The device was transferred to a vacuum filtration beaker, and 100° C. NMP was pulled from the "bottom side" to the "top side" (evaporated side) of the device with a pressure of roughly −25 inHg. The device was then removed and placed in a beaker of 100° C. NMP in an ultrasonic bath for several seconds to remove any remaining gold on the surface of the membrane. The membrane was saturated with isopropanol and baked on a hot plate at 60° C. for 30 minutes.

Second Evaporation

The second evaporation created the ground layer of the membrane, which included a total thickness of 80 nm of titanium and gold. The ground layer for this device was a continuous layer covering the entire membrane. Therefore further photolithography was unnecessary.

The devices were inverted (bottom side up) and returned to evaporator. The ground electrode was evaporated to the bottom of the device without a pattern (complete coverage) using the same recipe as the patterned electrode above. The evaporator was pumped to a vacuum of at least $4\times10^{-6}$ torr. Titanium was soaked in the e-beam for 3 minutes until it was sufficiently melted and evaporating. 2.5 nm of titanium was evaporated at a rate of no more than 0.6 Angstroms/s. Gold was then evaporated after a 3 minute soak to ensure uniform evaporation of material. 77.5 nm of gold was deposited at a rate of no more than 1.1 Angstroms/s. Samples were then allowed to cool in vacuum before being removed.

Annular Ring Removal

The polymer annular ring was then removed by heating a scalpel blade with a Bunsen burner, and carefully scraping the polymer ring off of the topside surface. The annular ring provided support for the devices up to this point, but caused the membrane to cup after heating and lift-off processing. The ring was removed at this point to provide a planar surface.

Microwell Attachment

Microwell molds were created using standard stamping methods. Stamp depth was measured at 260 kA on a profilometer. Polystyrene was prepared by mixing 15% polystyrene solution in anisole. The solution was then filtered through a 450 nm Teflon filter. The stamp was "loaded" with roughly one millimeter of polystyrene solution and vacuumed for 1 minute at roughly −25 inHg. The stamp was then spin coated at 3500 RPM for 60 seconds.

For this device, the 3×3 microwell alignment was attained by laminating the microwells onto the alumina membrane instead of stamping. By laminating, the microwell sheet could be aligned with the electrodes underneath, and then be heated to permanently adhere the microwells.

The 25 micron polystyrene sheet was then removed from the stamp with a set of tweezers, and placed in contact with the membrane. Adjustments were made to roughly align the electrodes and the microwells. The membrane was then brought into contact with a hotplate at 130° C. The polystyrene turned dark where it wetted the membrane. When the microwell structure had fully wetted the membrane, the device was removed from the hotplate. This took less than 30 seconds.

Microfluidic Attachment

The microfluidic channels were prepared by casting PDMS against a mold. The microfluidic channels were then punched with an 18 gauge needle blunted with a rotary tool equipped with a metal cutting blade. A glass slide was prepared by spinning Sylgard 184 at 4000 RPM for one minute, coating the slide. The 19 channel microfluidic pattern was brought into contact with the glass slide, and pressure was applied at roughly 2.9 PSI for 5 minutes. The microfluidic layer was removed and set aside to allow the Sylgard to flow for 25 minutes. The device was then brought into contact with the membrane, and pressure was applied at 8.5 PSI on a hotplate at 60° C. for one hour.

Ground Attachment and Device Potting

An electrically conductive epoxy was prepared and used to attach wire leads to the ground layer of the device. The epoxy was baked in an oven for 4 hours at 60° C. The device was then potted with T-2 Silastic to mechanically support the alumina membrane. PDMS was flowed over the exposed edges of the alumina membrane, cured at 60° C., and trimmed. The microfluidic inlets were protected by covering them with a small piece of brown packing tape to which PDMS could not adhere.

Lead Attachment and Electrical Isolation

An electrically conductive epoxy was prepared in a 1:1 ratio, and used to attach leads to the 19 individual contact sites of the topside electrodes resulting in 19 electrical leads. The device was then baked at 60° C. for 4 hours to cure the epoxy. The electrical connections were then electrically isolated using PDMS spread in tightly controlled lines over the connection sites.

Fluidic Attachment

Fluidic connections were made from cut 20 gauge needles bent at a 90 degree angle. One end of the tubing connection was attached to a piece of 1/32" Tygon tubing, and the other end was inserted into the microfluidic inlet. This was repeated for the opposing inlet on the same channel. Fluid was drawn through the device via vacuum to test the fluid connections. This was done for a total of 38 tubes to connect the inlet and outlet of all 19 channels. No further potting or connections were required for the fluidics, though additional potting could be used to provide added mechanical support Device Flow Test The device was flow tested by reversing the leads (ground becomes positive, positive becomes ground) and pumping Fluorescein isothiocyanate (FITC) into the microfluidics for easy visualization. In these tests, the device was prepared by soaking the device in PBS (standard solution), and placing the device in a vacuum desiccator for one hour. Once the membrane was properly wetted, the same PBS solution was pumped through the microfluidics until continuous flow was reached. A bolus of 0.005% FITC was placed in contact with the top of the device and a voltage of between 0.8V and 1.1 V was applied. The FITC was detected using a Green Flourescent Protein fluorescent source and filter.

The devices and methods of the appended claims are not limited in scope by the specific devices and methods described herein, which are intended as illustrations of a few aspects of the claims. Any devices and methods that are functionally equivalent are intended to fall within the scope of the claims. Various modifications of the devices and methods in addition to those shown and described herein are intended to fall within the scope of the appended claims. Further, while only certain representative devices and method steps disclosed herein are specifically described, other combinations of the devices, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A device comprising:
   (a) a nanoporous membrane having a top surface and a bottom surface;
   (b) a fluid source positioned in fluid contact with the bottom surface of the nanoporous membrane; and
   (c) a porous electrode patterned on one of the top or bottom surfaces of the nanoporous membrane so as to define a fluid delivery region in fluid contact with the top surface of the nanoporous membrane;
   wherein the porous electrode is configured such that, upon application of a potential bias across the nanoporous membrane, fluid flow is induced between the fluid source and the fluid delivery region.

2. The device of claim 1, wherein the fluid source comprises a delivery chamber.

3. The device of claim 1, wherein at least one of the fluid source or the fluid delivery region comprises a microfluidic channel.

4. The device of claim 1, wherein the porous electrode is patterned on the top surface of the nanoporous membrane so as to define the fluid delivery region in fluid contact with the top surface of the nanoporous membrane, or wherein the porous electrode is patterned on the bottom surface of the nanoporous membrane so as to define the fluid delivery region in fluid contact with the top surface of the nanoporous membrane.

5. The device of claim 1, wherein the fluid delivery region comprises a microwell.

6. The device of claim 5, wherein the microwell has a volume of from about 2 fL to about 1 mL.

7. The device of claim 5, wherein the microwell has a volume of from about 20 fL to about 1 µL.

8. The device of claim 1, wherein the fluid delivery region comprises a culture matrix.

9. The device of claim 1, wherein the fluid delivery region comprises a biological material.

10. The device of claim 9, wherein the biological material is selected from the group consisting of eukaryotic cells, prokaryotic cells, viruses, cell aggregates, tissues, and combinations thereof.

11. The device of claim 1, wherein the porous electrode further comprises
a plurality of porous electrodes patterned on one of the top or bottom surfaces of the nanoporous membrane so as to define a plurality of fluid delivery regions in fluid contact with the top surface of the nanoporous membrane;
wherein the plurality of porous electrodes are configured such that, upon application of a potential bias across the nanoporous membrane, fluid flow is induced between the fluid source and the plurality of fluid delivery regions.

12. The device of claim 11, wherein the plurality of porous electrodes are patterned the top surface of the nanoporous membrane so as to define the plurality of fluid delivery regions in fluid contact with the top surface of the nanoporous membrane.

13. The device of claim 11, wherein the plurality of porous electrodes are patterned on the bottom surface of the nanoporous membrane so as to define the plurality of fluid delivery regions in fluid contact with the top surface of the nanoporous membrane.

14. The device of claim 11, wherein the device further comprises a plurality of fluid sources, and wherein upon application of a potential bias across the nanoporous membrane, the plurality of fluid delivery regions are fluidly connected to the plurality of fluid sources.

15. The device of claim 11, wherein the fluid delivery regions are configured as a matrix which comprises:
(a) two or more rows of fluid delivery regions, each row of fluid delivery regions comprising a plurality of fluid delivery regions; and
(b) two or more columns of fluid delivery regions, each column of fluid delivery regions comprising a plurality of fluid delivery regions.

16. The device of claim 15, wherein upon application of a potential bias across the nanoporous membrane, the plurality of fluid delivery regions in each row of fluid delivery regions are fluidly connected to the same fluid source.

17. The device of claim 1, wherein the porous electrode further comprises:
a plurality of parallel linear electrodes patterned on the bottom surface of the nanoporous membrane; and
a plurality of parallel linear electrodes patterned on the top surface of the nanoporous membrane,
wherein the plurality of parallel linear electrodes patterned on the bottom surface of the nanoporous membrane and the plurality of parallel linear electrodes patterned on the top surface of the nanoporous membrane are substantially orthogonal so as to define the plurality of fluid delivery regions in fluid contact with the top surface of the nanoporous membrane, and
wherein the plurality of parallel linear electrodes patterned on the bottom surface of the nanoporous membrane and the plurality of parallel linear electrodes patterned on the top surface of the nanoporous membrane are configured such that, upon application of a potential bias across the nanoporous membrane, fluid flow is induced between the fluid source and one of the fluid delivery regions.

18. The device of claim 1, wherein the device further comprises:
a plurality of parallel microfluidic channels positioned in fluid contact with the bottom surface of the nanoporous membrane,
wherein the porous electrode further comprises a plurality of parallel linear electrodes patterned on the top surface of the nanoporous membrane,
wherein the plurality of parallel microfluidic channels and the plurality of parallel linear electrodes are substantially orthogonal so as to define the plurality of fluid delivery regions in fluid contact with the top surface of the nanoporous membrane, and
wherein the plurality of parallel microfluidic channels and the plurality of parallel linear electrodes are configured such that, upon application of a potential bias across the nanoporous membrane, fluid flow is induced between one of the microfluidic channels and one of the fluid delivery regions.

19. The device of claim 1, wherein upon application of a potential bias across the nanoporous membrane, fluid flow is induced between the fluid source and the fluid delivery region at a flow rate of from about 0.025 fL/ms to about 0.50 fL/ms.

20. A method for delivering a defined volume of a solution to a fluid delivery region comprising
(a) providing the solution in a fluid source of the device defined by claim 1; and
(b) applying a potential bias across the nanoporous membrane for a period of time to induce flow of the solution from the fluid source to the fluid delivery region;
wherein the potential bias and period of time are selected to induce the flow of a defined volume of the solution from the fluid source to the fluid delivery region.

* * * * *